United States Patent [19]

Rabi et al.

[11] 4,434,235
[45] Feb. 28, 1984

[54] METHOD AND APPARATUS FOR DETECTING NITRITE IONS IN FLUIDS

[75] Inventors: Tavassa Rabi; Eugen Szekely, both of Beer Sheva, Israel

[73] Assignee: Ben Gurion University of the Negev Research and Development Authority, Beer Sheva, Israel

[21] Appl. No.: 338,837

[22] Filed: Jan. 12, 1982

[30] Foreign Application Priority Data

Jan. 21, 1981 [IL] Israel ........................ 61951

[51] Int. Cl.³ .................... G01N 33/52; G01N 33/84
[52] U.S. Cl. .................................. 436/110; 422/58; 422/61; 422/101; 435/37; 436/175
[58] Field of Search ................ 23/230 B; 422/58, 59, 422/101, 102, 61; 435/37; 436/110, 175

[56] References Cited

U.S. PATENT DOCUMENTS

| | | | |
|---|---|---|---|
| 3,446,596 | 5/1969 | Salivar | 436/110 |
| 3,634,198 | 1/1972 | Truhan | 435/37 |
| 3,645,853 | 2/1972 | Kronish | 435/37 X |
| 3,712,853 | 1/1973 | Rittersdorf | 435/37 |
| 3,718,543 | 2/1973 | Lagomarsino | 195/99 |
| 3,785,929 | 1/1974 | Kronish | 435/37 |
| 3,817,705 | 6/1974 | Stein | 436/110 |
| 3,832,141 | 8/1974 | Haldopoulos | 422/101 |
| 4,292,042 | 9/1981 | Kimble | 436/175 X |
| 4,348,374 | 9/1982 | Chau | 23/230 B |

FOREIGN PATENT DOCUMENTS 2141487 2/1973 Fed. Rep. of Germany .

OTHER PUBLICATIONS

E. Szekely, Talanta, 15, 795-801 (1968).
Chemical Abstracts, 95:128658z (Oct. 1981).

*Primary Examiner*—Sidney Marantz
*Attorney, Agent, or Firm*—Oblon, Fisher, Spivak, McClelland & Maier

[57] ABSTRACT

A method for detecting the presence of nitrite ions in fluids by pretreating nitrite containing fluids to enhance the detectability with nitrite detecting reagents of the nitrite ions therein, which pretreatment step comprises passing the nitrite containing fluids through activated charcoal prior to combination with a nitrite detection reagent.

Also a test kit for carrying out the above method.

13 Claims, 3 Drawing Figures

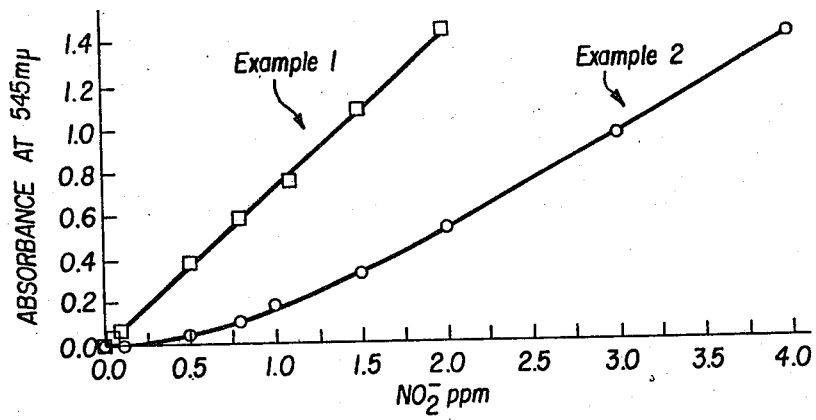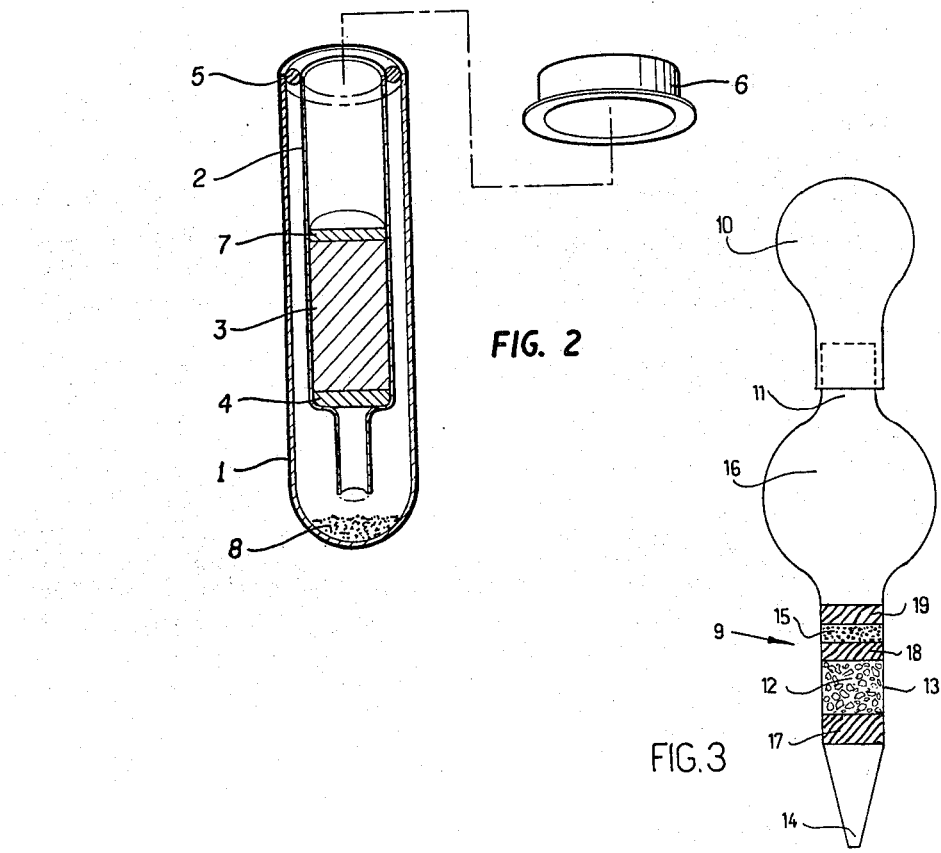

METHOD AND APPARATUS FOR DETECTING NITRITE IONS IN FLUIDS

The present invention relates to a method and apparatus for detecting nitrite ions in fluids. More particularly the present invention relates to a method for detecting the presence of nitrite ions in fluids involving the pretreatment of such fluids to enhance the detectibility, with nitrite detecting reagents, of the nitrite ions therein and test kits for carrying out said method. An important application of the present invention is its use in a method for detecting nitrate reducing bacteria in fluids derived from or containing organic matter by testing said fluids for the presence of nitrate ions.

The present invention is also directed to the use of a specially preferred nitrite detecting reagent in the method and apparatus described herein which reagent has been developed and found to be of increased sensitivity and stability in the present context.

It is to be noted however that the method of the present invention can be used in combination with many of the presently marketed nitrite detecting reagents to increase their accuracy and sensitivity to nitrite ions.

As will be described and explained in more detail hereinafter, this increased sensitivity, which is one of the advantageous characteristics of the method of the present invention, enables its use in the routine diagnosis of bacteriuria and in the follow-up of urinary tract infection in high risk groups such as diabetics, pregnant women, children, premature infants and patients with catheterization of the urinary tract. Furthermore, the increased sensitivity also enables detection of bacteriuria in urine samples taken throughout the day and not necessarily first morning urine samples (after overnight bladder incubation), which are recommended for the other currently used nitrite tests.

As is known, detection of urinary track infection or bacteriuria by the conventional urine culture method is currently the most reliable way of diagnosing this disease. However, this method has certain drawbacks, i.e. the time required for the test, the fact that it must be carried out by trained personnel, and consequently, its high cost. Thus, the routine use of the culture test is generally restricted to cases where a general urine test has already indicated the presence of protein or pyuria (white blood cells in the urine). This restricted use may not be clinically justified as research suggests that pyuria is not always a reliable indication of bacteriuria and vice-versa: there are instances where bacteriuria is not accompanied by pyuria or by protein and likewise there are cases where pyuria is found in the absence of bacteriuria.

A rapid cheap, reliable screening test is, therefore, important for use in the routine diagnosis of bacteriuria in a variety of patient populations, including: diabetics, pregnant women, children, premature infants and patients with catheterizations. Similarly a screening test is important for routine follow-up of patients with recurring urinary tract infections.

Several diagnostic tests have been made available which claim ability to detect clinically significant bacteriuria ($10^5$ bacteria/ml or more). A few of these techniques are based on a single reaction of urine culture growth. Other methods are based on detection of nitrite in the urine of bacteriuric patients (stat test—T.J.LIe, J. Clin., Path. 21, 443 (1968), bac U test—C. M. Kunin et al. J. Am. Med. Assoc. 231, 1349 (1975) and the more recent DIR Microstix test. C. M. Moffat et al. Applied Microbiol. 28, 95 (1974), Multistix test I. J. Skelton et al. Med. J. Aust. 1, 882, (1977), and BM test, J. P. Guinguard et al. Lancet 7, 47 (1978). The nitrite test is based on the fact that the urinary tract pathogens are usually of the enteric gram negative group. These bacteria have the ability to reduce the nitrate, which naturally occurs in urine, to nitrite. Other techniques combine both of the above-mentioned methods (Craig, W. A. et al. J. Appld. Microbiol. 26, 196, (1973), C. M. Moffat et al. J. Appld. Microbiol. 28, 95, (1974) and Marr, T. J. et al., A. J. Dis. Child., 126, 940, (1975).

The currently accepted chemical tests are all based on the well known Griess Ilosvay reaction which is based on two processes: Diazotation of sulfanilic acid and coupling with alpha-naphthyl amine. Because this coupling agent is a carcinogen, some variants were developed (N. G. Burtol et al. Analyst 94, 585 (1969).

It has been noted however and will be shown in the comparative examples hereinafter that in the above mentioned tests often the results obtained are not satisfactory and/or conclusive due to the difficulty in detecting the product color or due to inadequate reliability, particularly when the urine samples are collected randomly.

With the above in mind there is now provided in accordance with the present invention a method for detecting the presence of nitrate ions in fluids comprising pretreating nitrite containing fluids to enhance the detectability with nitrite detecting reagents of the nitrite ions therein, said pretreatment step comprising passing said fluid through activated charcoal prior to combination with a nitrite detection reagent.

The present invention also provides a first test kit for carrying out said method for the detection of the presence of nitrite ions in fluids said test kit comprising an open ended inner tube within an outer tube chamber having an air space between said tubes, said inner tube containing activated charcoal and filtering means and said outer tube chamber containing a nitrite detection reagent, wherein liquid introduced into said test kit passes through said inner tube and the activated charcoal therein before entering the air space between said tubes for combination with said nitrite detection reagent.

Also provided is a second test kit for carrying out said method for the detection of the presence of nitrite ions in fluids said test kit comprising a tube having a suction bulb at one end thereof and containing activated charcoal positioned and held inside a section of said tube wherein fluid sucked into said tube from the other end thereof passes through said activated charcoal.

A preferred reagent for detecting nitrite in accordance with the method of the present invention comprises the following ingredients:

(a) 4,4' sulfonyldianiline (as diazotizing amine)
(b) N-(1-naphthyl)-ethylenediamine or its salt (coupling agent) and
(c) organic polycarboxylic acid (as buffer).

The proportions of ingredients can vary widely but it has been found that the following is an especially preferred useful range:

(a) 0.5–5 g-4,4-sulfonyldianiline
(b) 0.1–1 g N-(1-naphthyl)-ethylene diamine, dihydrochloride and (c) 50–1000 g organic polycarboxylic acid.

Organic polycarboxylic acids which may be used as components of the reagent are, for example, adipic acid, citric acid, glutamic acid, malic acid, malonic acid, oxalic acid, succinic acid, tartaric acid and many other similar acids. Citric acid is, however, preferred. It is understood that the reagent is not limited to the above given composition on the contrary it is intended to cover all alternatives and modifications and equivalents as may be included within the scope of the invention.

The reagent can be mixed and used in solid form or prepared in solution. Water, water miscible alcohol, or mixtures of these may be used as solvent for the reagent as may dilute hydrochloric acid. As is recognized, previously disclosed methods for detecting nitrite ions in urine use reagents in acidic solutions and as such they are rather unstable. Attempts to stabilize said reagents have not been fully satisfactory. In contradistinction to said prior art reagents, the reagent of the instant method is preferably a dry powder blend which can be stored for extended periods and when dissolved in water, the solution is stable for two months, at least.

In U.S. Pat. Nos. 3,634,198; 3,645,853; 3,712,853; 3,718,543 and 3,785,929 as well as in German Pat. No. 2141487 and in the article in Talanta 15 795–801(1968) there are described nitrite detection reagents and tests, however, none of said publication teach or suggest the pretreatment step of the present invention which can even be used to improve the sensitivity of tests described therein.

While activated charcoal has undeniably been known and used for decades as a filtering media its use and application in the present method has heretofore not been taught or suggested despite the widefelt need for improvement in this very commercialized medical area.

Furthermore the activated charcoal when used in the present method and apparatus has been found to have many unexpected advantages including eliminating interference previously experienced due to various factors such as increasing pH of the urine, increasing darkness of the urine, hematuria, the orange color of the urine of patients treated with pharmaceuticals, etc.

The activated charcoal also serves to clarify and decolorize a turbid and/or colored sampled before combination of the sample with a nitrite detecting reagent although other decolorizing agents can optionally be used in conjunction with said activated charcoal.

It has now also been found that for best results in the method of the present invention the charcoal is preferably pretreated by washing with dilute aqueous alkali base or basic buffer and drying. This pretreatment of the charcoal before use in the present invention appears to insure the most reproducible results.

Pretreatment of the activated charcoal has been performed by stirring the charcoal with various basic solutions such as sodium hydroxide, sodium carbonate, disodium acid phosphate, sodium citrate, sodium glutamate, borax, or blending it with MgO, etc. Stirring for 5–10 minutes is usually sufficient after which the charcoal is filtered and dried.

It has been also found that the above mentioned preferred reagent used in the method and apparatus of the present invention is sensitive to air when it is contaminated with nitrogen oxides. Consequently, it should be kept in a sealed container as described hereinafter. Similarly when activated charcoal undergoes treatment with base, it also tends to absorb nitrogen oxides from the air and then a color might develop even with a blank of nitrite free water. For this reason, said activated charcoal should also be kept in a closed container or kit as described hereinafter. The test of this invention can be performed in the conventional manner known in the art. The reagent may be impregnated with or without decolorizing material into paper, cloth or plastic strips for use as an indicator. It may alternatively be formulated as a dip stick or in some other known form.

The presence of nitrate reducing bacteria or nitrite is indicated with said reagent by the development of a pinkish-violet color, the intensity of which can be measured instrumentally at $\lambda$ max 545 m$_{82}$ or compared visually. The intensity of the color is proportional to the nitrite concentration and is stable for several hours.

Since the preferred method of the present invention involves the pretreatment with charcoal of samples prior to testing with the reagent, the present invention is also directing to several novel kits for performing said pretreatment of the samples in an inexpensive and convenient manner as mentioned hereinbefore and as described more fully with reference to the figures hereinafter.

This kit comprises an open ended inner tube within an outer tube chamber with an air space between the two. The inner tube contains a decolorizing material such as activated charcoal and suitable filtering means and the outer tube chamber contains the reagent.

In order that the invention may be more fully understood, it will now be described in connection with certain preferred embodiments in the following examples and with reference to the following illustrative figures, it being understood that it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars described are by way of example and for purposes of illustrative discussion of preferred embodiments of the present invention only and are presented in the cause of providing what is believed to be the most useful and readily understood description of procedures as well as of the principles and conceptual aspects of the invention.

In the drawings:

FIG. 1 shows the absorption curves for samples in examples 1 and 2 hereinafter;

FIG. 2 shows a test tube kit for carrying out the method of the present invention; and FIG. 3 shows another embodiments of a test kit for carrying out the method of the present invention.

EXAMPLE 1

Nitrite reagent was prepared as follows:

1 g N-(1-naphthyl)amine ethylenediamine dihydrochloride was mixed with 5 g 4,4'-sulfonyldianiline and 1000 g citric acid. The mixture was thoroughly blended, 50 g of solid reagent was dissolved in water to make up 100 ml of solution, and the solution was used for the tests.

Samples of about 3 ml of urine containing varying amounts of added nitrite were placed in a test tube and 0.25 g activated charcoal power (acid washed) was added. The test tube was thoroughly shaken and the contents filtered into another test tube through Whatman No. 42 filter paper. The filtrate was a clear colorless liquid. 5 drops of reagent were added. A pinkish-violet color developed immediately and the maximum intensity was obtained in a few minutes for samples containing 0.05 ppm nitrite ion or more per ml.

COMPARATIVE EXAMPLE 2

Samples of 3 ml of urine containing the same varying amounts of added nitrite as in example 1 were treated directly with 4 drops of reagent without undergoing charcoal pretreatment. A deep yellow color developed in the sample containing 0.5 ppm nitrite and a pinkish-violet color developed in 1 to 2 minutes in all samples having more than 1.0 ppm nitrite present.

As stated, FIG. 1 shows the absorption curves for the samples tested in example 1 and 2 containing between 0.05 and 2.5 ppm nitrite.

EXAMPLE 3 AND COMPARATIVE EXAMPLE 4

Samples of urine having added nitrite, as in examples 1 and 2, were tested with Microstix reagent strips (a commercial test for nitrite in urine) manufactured by Ames Co. Inc.

In Example 3 a charcoal decolorized urine sample used in Example 1, gave a detectable color with the Microstix only at concentrations above 3 ppm nitrite ions while in comparative Example 4 the untreated urine showed a detectable color only above 5 ppm nitrite ions with Microstix strips.

Table 1 shows the colors obtained in Examples 1, 2, 3 and 4 at the various concentrations of nitrite from 0.05 to 100 ppm.

From Table 1 it can be seen that while the preferred reagent of the present invention is in itself much more sensitive than the commercial Microstix strips the pretreatment step of the present invention increases its sensitivity by about 10 times while also increasing the sensitivity of the Microstix by about 2 times.

The combined results seen from comparing Example 1 with Example 4 shows that whereas with the normal microstix test a pale pink color appears only at a concentration of 4–5 ppm of nitrite, the preferred pretreatment step and reagent of the present invention was able to clearly detect 0.05 ppm of nitrite.

TABLE 1

| Charcoal treated urine | | ppm | Untreated urine | |
|---|---|---|---|---|
| Example 1 | Example 3 | $NO_2^-$ | Comparative Example 2 | Comparative Example 4 |
| pale pink | no change | 0.05 | no change | no change |
| pale pink | " | 0.1 | " | " |
| pink | " | 0.5 | " | " |
| light violet | " | 0.8 | pinkish-orange | " |
| violet | " | 1.0 | pale pink | " |
| violet | " | 1.5 | pink | " |
| violet | " | 2 | pink | " |
| violet | barely visible pink | 3 | pink | " |
| dark violet | pale pink | 4 | dark pink | " |
| dark violet | pale pink | 5 | violet | very pale pink |
| very dark violet | pink | 10 | dark violet | pale pink |
| reddish violet | dark pink | 20 | very dark violet | pink |
| reddish violet | dark pink | 30 | reddish violet | pink |
| reddish violet | dark pink | 40 | reddish violet | dark pink |
| reddish purple | dark pink | 60 | reddish purple | dark pink |

TABLE 1-continued

| Charcoal treated urine | | ppm | Untreated urine | |
|---|---|---|---|---|
| Example 1 | Example 3 | $NO_2^-$ | Comparative Example 2 | Comparative Example 4 |
| purple | dark pink | 100 | reddish purple | dark pink |

The following tables further demonstrate the improvements in sensitivity and accuracy obtainable using the pretreatment method of the present invention with the commercial Microstix and N-Multistix tests of Ames Co. and the commercial BN-test (Manufactured by Boehringer John C. H.).

TABLE II

| | | | Microstix test | |
|---|---|---|---|---|
| Organism | bacteria/nl | SRN test ppm $NO_2^-$ | before treatment of fluid with charcoal | after treatment of fluid with charcoal |
| coli | $3 \times 10^7$ | 4 | orange | + |
| coli | $10^8$ | 7.5 | orange | + |
| coli | $3 \times 10^6$ | 0.5 | — | —* |
| Alrobacter | $3 \times 10^7$ | 10 | — | + |
| coli | $3 \times 10^8$ | 7.5 | — | + |
| coli | $5 \times 10^5$ | 2 | — | —* |
| coli | $3 \times 10^7$ | 1 | — | —* |
| coli | $5 \times 10^5$ | 1 | — | —* |
| coli | $1.2 \times 10^7$ | 4 | — | + |
| coli | $4 \times 10^6$ | 2 | — | —* |
| coli | $6 \times 10^6$ | 2 | orange | —* |
| coli | $8 \times 10^7$ | 4 | — | + |
| coli | $4 \times 10^7$ | 4 | — | + |
| coli | $2 \times 10^8$ | 10 | orange | + |
| coli | $3 \times 10^7$ | 20 | (±) | + |
| coli | $10^7$ | 20 | orange | + |
| coli | $10^8$ | 7 | orange | + |

TABLE III

| | | | N-Multistix test | |
|---|---|---|---|---|
| Organism | Bacteria/nl | SRN test ppm $NO_2$ | Before treatment | After treatment |
| coli | $3 \times 10^7$ | 4 | orange | + |
| coli | $10^8$ | 7.5 | orange-pinkish | + |
| coli | $3 \times 10^6$ | 0.5 | — | —* |
| coli | $5 \times 10^5$ | 2 | — | + |
| coli | $5 \times 10^5$ | 1 | — | —* |
| coli | $6 \times 10^8$ | 7 | orange | + |
| coli | $4 \times 10^6$ | 2 | — | + |
| coli | $6 \times 10^6$ | 2 | orange | + |
| coli | $10^8$ | 7 | orange | + |

TABLE IV

| | | | BM-test | |
|---|---|---|---|---|
| Organism | Bacteria/nl | SRN test ppm $NO_2^-$ | before treatment | After treatment |
| coli | $3 \times 10^7$ | 4 | orange | + |
| coli | $10^8$ | 7 | orange-pinkish | + |
| coli | $2 \times 10^6$ | 0.5 | — | + |
| coli | $5 \times 10^5$ | 0.5 | — | + |
| coli | $5 \times 10^5$ | 0.8 | ± | + |
| coli | $6 \times 10^6$ | 0.8 | ± | + |
| coli | $6 \times 10^8$ | 7 | orange pinkish | + |
| coli | $5 \times 10^6$ | 0.5 | — | + |
| coli | $2 \times 10^8$ | 10 | orange pinkish | + |
| coli | $2 \times 10^6$ | 0.8 | — | + |
| coli | $10^7$ | >20 | orange pinkish | + |
| coli | $10^8$ | 7 | orange pinkish | + |

In the above tables orange and orange-pinkish are the color of the urine due to medicine: (—) indicates lack of positive reaction to nitrites; (+) indicates a positive nitrite reaction: (±) indicates a weak or faint nitrite reaction; and (*) indicates lack of reaction to nitrate even after treatment of fluid simply because the concentration of $NO_2^-$ was below the sensitivity range of the test.

As can be seen in almost all instances treatment of the urine with activated charcoal before combination with the nitrite detecting means resulted in improved sensitivity and reliability of the test. Furthermore the activated charcoal besides eliminating chemical interfering means also serves to decolorize samples thus preventing false positive test results using said other commercial testing means as illustrated in Table V hereinafter wherein urine samples free of nitrites, however colored due to medicine ingested by the patients were tested and gave false positive results unless pretreated according to the present invention.

TABLE V

| Urine color | bact/ml | SRN test ppm $NO_2^-$ | BM test bt | at | Microstix test bt | at | N-Multistix test bt | at |
|---|---|---|---|---|---|---|---|---|
| orange | 0 | 0 | OP | — | OP | — | OP | — |
| red | 0 | 0 | OR | — | OR | — | OR | — |
| orange-red | 0 | 0 | OR | — | OR | — | OR | — |
| orange | 0 | 0 | OP | — | O | — | OP | — |
| orange | 0 | 0 | OP | — | O | — | OP | — |
| orange | 0 | 0 | OP | — | O | — | OP | — | bt = before treatment
at = after treatment
OP = orange-pinkish
OR = orange reddish As stated above while commercial activated charcoal may be used in the method and apparatus of the present invention it has been surprisingly found that acid washed activated charcoal, stirred with an aqueous solution of a base for about 1–10 minutes and then filtered and dried gives superior results with the use of base treated activated charcoal resulting in more sensitive nitrite detection and more reproducable determination than with untreated charcoal.

EXAMPLE 5

5 g activated charcoal was stirred for 3 minutes in a 0.5 M borax solution, filtered, dried at 40° C. in a vacuum oven overnight and stored in a tightly sealed container.

Samples of normal urine containing various amounts of added nitrite ions were passed through treated and untreated charcoal filters and then tested with the preferred nitrite detection reagent. The results of said multiple tests are tabulated in Table VI.

TABLE VI

| Urine samples | ppm nitrites added to urine samples 1 and 2 | Untreated activated charcoal (in triplicates) | Treated charcoal (in triplicates) |
|---|---|---|---|
| 1 | 0.1 | 0 | 0.1 |
|   |   | 0 | 0.1 |
|   |   | 0.05 | 0.1 |
| 2 |   | 0 | 0.1 |
|   |   | 0 | 0.1 |
|   |   | 0 | 0.1 |
| 1 | 0.5 | 0.05 | 0.5 |
|   |   | 0.1 | 0.5 |
|   |   | 0.2 | 0.5 |
| 2 |   | 0.01 | 0.5 |
|   |   | 0.1 | 0.5 |
|   |   | 0.3 | 0.5 |
| 1 | 1 | 0.1 | 1 |
|   |   | 0.5 | 1 |

TABLE VI-continued

| Urine samples | ppm nitrites added to urine samples 1 and 2 | Untreated activated charcoal (in triplicates) | Treated charcoal (in triplicates) |
|---|---|---|---|
|   |   | 0.8 | 1 |
| 2 |   | 0.5 | 1 |
|   |   | 0.5 | 1 |
|   |   | 0.8 | 1 |
| 1 | 1.5 | 0.5 | 1.5 |
|   |   | 0.5 | 1.5 |
|   |   | 0.8 | 1.5 |
| 2 |   | 0.3 | 1.5 |
|   |   | 0.8 | 1.5 |
|   |   | 1 | 1.5 |
| 1 | 5 | 1 | 5 |
|   |   | 2 | 5 |
|   |   | 2 | 5 |
| 2 |   | 0.5 | 5 |
|   |   | 2 | 5 |
|   |   | 3 | 5 |
| 1 | 10 | 4 | 10 |
|   |   | 5 | 10 |
|   |   | 5 | 10 |
| 2 |   | 5 | 10 |
|   |   | 7 | 10 |
|   |   | 7 | 10 |
| 1 | 20 | 8 | 20 |
|   |   | 8 | 20 |
|   |   | 10 | 20 |
| 2 |   | 8 | 20 |
|   |   | 10 | 20 |
|   |   | 10 | 20 |

Referring now briefly to FIG. 2 there is illustrated one embodiment of a test kit adapted to facilitate the carrying out of the method of the present invention comprising an outer tube chamber 1, an inner tube 2 containing base treated activated charcoal 3, a filter 4, means in the form of an O-ring 5 for maintaining an air space between the tubes and for allowing equalization of atmospheric pressure between the inner 2 and outer 1 tubes and a cap 6 for closing the tube. An additional filter or cotton wad 7 is also provided for helping to maintain the activated charcoal in place.

The kit and its component tubes can be made of transparent plastic or glass and are inexpensive enough to manufacture to make the kit disposable.

In practicing the method of the present invention with this kit, a sample to be tested is introduced into the inner tube, passes through the activated charcoal, then through the filter into the outer tube 1 where it reacts with the nitrite reagent 8. If nitrate is present in the sample the characteristic pink-violet color develops and reaches maximum intensity in a few minutes.

A filtering kit superficially similar in structure to the kit described with reference to FIG. 2 appears in U.S. Pat. No. 3,832,141 however said patent of course neither teaches nor suggests a kit specifically adapted for carrying out the method of the present invention.

Referring now to FIG. 3 there is shown another even simpler kit for carrying out the method of the present invention.

In its simplest from said kit comprises a tube 9 having a suction bulb 10 at one end 11 thereof and containing activated charcoal 12 positioned and held inside a section 13 of said tube wherein fluid sucked into said tube from the other end 14 thereof passes through said activated charcoal and can be combined with any nitrate detecting medium.

In its preferred form said kit is self-contained and further comprises a dry powdered water soluble nitrite detecting reagent 15 positioned between said charcoal 12 and said bulb 10 as well as having an enlarged chamber 16 between said reagent 15 and said bulb 10 wherein fluid sucked into said tube by means of said bulb first passes through said charcoal and then through said reagent for collection and observation in said enlarged chamber.

Preferably, as shown said activated charcoal 12 and nitrite detecting reagent 15 are positioned and held in said tube by bounding liquid-permeable solid-filtering means such as cotton plugs 17, 18 and 19 and preferably said reagent 15 comprises 4,4'-sulfonyldianiline; N-(1-naphthyl)-ethylene diamine or its salts and an organic polycarboxylic acid in dry powdered form.

The following Examples further illustrate the application of the method of the present invention.

EXAMPLE 6

Normal urine samples to which known amounts of nitrites have been added were tested with the kit of FIG. 2 of the present invention, in the following procedure: A few ml of urine were transferred into the inner tube of the kit to pass through the activated charcoal and cottom filter thereof into the external tube containing the preferred reagent of the present invention. A characteristic pinkish-violet color developed whenever nitrite in amounts have 0.05 ppm were present in the samples. Maximum intensity of color is obtained in a few minutes, proportional to the amount of the nitrite ions.

Full recuperation of the added nitrite amounts in the urine was obtained.

Test on randomly collected urine specimens suspected for bacteriuria taken from clinical and Hospital laboratories in Beer Sheva were conducted with the nitrite test of the present invention and with the conventional urine culture method. The various pale yellow to dark and/or turbid, slightly acidic, neutral or slightly alkaline urine samples were tested by using the kit of the present invention in the procedure described above.

A good correlation between the culture method and the method of the present invention was obtained.

Application for this inventive method in the detection of nitrite ions in various colored and/or turbid samples derived from or containing organic matter such as extracts of soils and plants, vegetables, fruits, canned meats and salami, etc. is illustrated in Example 7.

EXAMPLE 7

10 grams of fresh salami were added to 50 cc distilled water and homogenized. To the resulting homogeneous mixture an additional 50 cc distilled water was added.

A few ml of the sedimented sample solution has been transferred into the inner tube of the kit of the present invention and following the procedure as given in Example 6, known amounts of nitrites were added to the samples and full detection and recovery of the added nitrile amounts was obtained.

It will be evident to those skilled in the art that the invention is not limited to the details of the foregoing illustrative embodiments and examples and that the present invention may be embodied in other specific forms without departing from the essential attributes thereof. It is, therefore, desired that the present examples and embodiments be considered in all respects as illustrative and not restrictive, reference being made to the appended claims, rather than to the foregoing description, and all changes which come with the meaning and range of equivalency of the claims are, therefore, intended to be embraced therein.

What is claimed is:

1. A method for detecting the presence of nitrite ions in fluids comprising pretreating nitrite containing fluids to enhance the detectability of the nitrite ions therein with a nitrite detecting reagent, said pretreatment step comprising passing said fluid through activated charcoal prior to combination with said nitrite detection reagent.

2. A method according to claim 1 wherein said activated charcoal is base treated prior to use.

3. A method according to claim 2 wherein said activated charcoal is treated with borax prior to use.

4. A method according to claim 3 comprising passing said fluid through a column of activated charcoal prior to combination with said nitrite detection reagent.

5. A method for detecting nitrate reducing bacteria in fluids derived from or containing organic matter by testing said fluids for nitrite ions in accordance with the method of claim 1, wherein after passing said fluid through said activated charcoal said treated fluid is combined with said nitrite detection reagent.

6. A method according to claim 5 wherein said fluid is urine.

7. A method accordance with claim 1, wherein the reagent for nitrite detection comprises
   (a) 0.5–5 parts 4,4'-sulfonyldianiline
   (b) 0.1–1 part N-(1-naphthyl)-ethylene diamine or its salts and
   (c) 50–1000 parts organic polycarboxylic acid.

8. A test kit for carrying out the method of claim 1 for the detection of the presence of nitrate ions in fluids said test kit comprising an open ended inner tube within an outer tube chamber having an air space between said tubes, said inner tube containing activated charcoal and filtering means and said outer tube chamber containing said nitrite detection reagent wherein liquid introduced into said test kit passes through said inner tube and the activated charcoal therein before entering the air space between said tubes for combination with said nitrite detection reagent.

9. A test kit for detecting nitrite ions according to claim 8 comprising an open ended inner tube within an outer tube chamber having an air space between said tubes, said inner tube containing activated charcoal and said outer tube chamber containing said dry powered water-soluble nitrite reagent comprising 4,4'-sulfonyldianiline, N-(1-naphthyl)-ethylene diamine or its salts and an organic polycarboxylic acid.

10. A test kit for carrying out the method of claim 1 for the detection of the presence of nitrite ions in fluids said test kit comprising a tube having a suction bulb at one end thereof and containing activated charcoal and nitrite detection reagent separately positioned and held inside a section of said tube wherein fluid sucked into said tube from the other end thereof passes sequentially through said activated charcoal and nitrite detection reagent.

11. A test kit according to claim 10 wherein said nitrite detecting reagent is positioned between said charcoal and said bulb and further comprising an enlarged chamber between said reagent and said bulb wherein fluid sucked into said tube by means of said bulb first passes through said charcoal and then through said reagent for collection and observation in said enlarged chamber.

12. A test kit according to claim 11 wherein said activated charcoal and nitrite detecting reagent are positioned and held in said tube by bounding liquid-permeable solid filtering means.

13. A test kit according to claim 11 wherein said reagent comprises
(a) 4,4'-sulfonyldianiline
(b) N-(1-naphthyl)-ethylene diamine or its salts and
(c) organic polycarboxylic acid.

* * * * *